United States Patent
Bell et al.

(10) Patent No.: US 7,192,954 B2
(45) Date of Patent: Mar. 20, 2007

(54) MONOCYCLIC ANILIDE SPIROHYDANTOIN CGRP RECEPTOR ANTAGONISTS

(75) Inventors: Ian M. Bell, Harleysville, PA (US); Cory R. Theberge, King of Prussia, PA (US); Theresa M. Williams, Harleysville, PA (US); C. Blair Zartman, Hartfield, PA (US); Xu-Fang Zhang, Dresher, PA (US); Steven N. Gallicchio, Wyndmoor, PA (US)

(73) Assignee: Merck & Co., Inc., Rahway, NJ (US)

( * ) Notice: Subject to any disclaimer, the term of this patent is extended or adjusted under 35 U.S.C. 154(b) by 56 days.

(21) Appl. No.: 10/547,082

(22) PCT Filed: Mar. 10, 2004

(86) PCT No.: PCT/US2004/007678

§ 371 (c)(1),
(2), (4) Date: Aug. 26, 2005

(87) PCT Pub. No.: WO2004/083187

PCT Pub. Date: Sep. 30, 2004

(65) Prior Publication Data

US 2006/0148779 A1    Jul. 6, 2006

Related U.S. Application Data

(60) Provisional application No. 60/454,944, filed on Mar. 14, 2003.

(51) Int. Cl.
| | |
|---|---|
| A61K 31/4439 | (2006.01) |
| A61K 31/422 | (2006.01) |
| A61K 31/551 | (2006.01) |
| C07D 413/02 | (2006.01) |
| C07D 243/04 | (2006.01) |
| C07D 401/14 | (2006.01) |

(52) U.S. Cl. ................ 514/218; 514/278; 514/341; 514/376; 548/229; 546/274.4; 540/492

(58) Field of Classification Search ........... 514/218, 514/278, 341, 376; 548/229; 546/274.4; 540/492
See application file for complete search history.

(56) References Cited

U.S. PATENT DOCUMENTS 4,772,632 A    9/1988    Vistica

*Primary Examiner*—Kamal A. Saeed
*Assistant Examiner*—Jason M. Nolan
(74) *Attorney, Agent, or Firm*—David L. Rose; David Rubin

(57) ABSTRACT

The present invention is directed to compounds that are antagonists of CGRP receptors and that are useful in the treatment or prevention of diseases in which the CGRP is involved, such as headache, migraine and cluster headache. The invention is also directed to pharmaceutical compositions comprising these compounds and the use of these compounds and compositions in the prevention or treatment of such diseases in which CGRP is involved.

17 Claims, No Drawings

US 7,192,954 B2

MONOCYCLIC ANILIDE SPIROHYDANTOIN CGRP RECEPTOR ANTAGONISTS

CROSS REFERENCE TO RELATED APPLICATIONS

This application is the National Stage of International Application No. PCT/US2004/007678, filed 10 Mar. 2004 which claims the benefit under 35 U.S.C. 119(e) of U.S. Provisional Application No. 60/454,944, filed 14 Mar. 2003.

BACKGROUND OF THE INVENTION

CGRP (Calcitonin Gene-Related Peptide) is a naturally occurring 37-amino acid peptide that is generated by tissue-specific alternate processing of calcitonin messenger RNA and is widely distributed in the central and peripheral nervous system. CGRP is localized predominantly in sensory afferent and central neurons and mediates several biological actions, including vasodilation. CGRP is expressed in alpha- and beta-forms that vary by one and three amino acids in the rat and human, respectively. CGRP-alpha and CGRP-beta display similar biological properties. When released from the cell, CGRP initiates its biological responses by binding to specific cell surface receptors that are predominantly coupled to the activation of adenylyl cyclase. CGRP receptors have been identified and pharmacologically evaluated in several tissues and cells, including those of brain, cardiovascular, endothelial, and smooth muscle origin.

CGRP is a potent vasodilator that has been implicated in the pathology of cerebrovascular disorders such as migraine and cluster headache. In clinical studies, elevated levels of CGRP in the jugular vein were found to occur during migraine attacks (Goadsby et al., Ann. Neurol., 1990, 28, 183–187). CGRP activates receptors on the smooth muscle of intracranial vessels, leading to increased vasodilation, which is thought to be the major source of headache pain during migraine attacks (Lance, Headache Pathogenesis: Monoamines, Neuropeptides, Purines and Nitric Oxide, Lippincott-Raven Publishers, 1997, 3–9). The middle meningeal artery, the principle artery in the dura mater, is innervated by sensory fibers from the trigeminal ganglion which contain several neuropeptides, including CGRP. Trigeminal ganglion stimulation in the cat resulted in increased levels of CGRP, and in humans, activation of the trigeminal system caused facial flushing and increased levels of CGRP in the external jugular vein (Goadsby et al., Ann. Neurol., 1988, 23, 193–196). Electrical stimulation of the dura mater in rats increased the diameter of the middle meningeal artery, an effect that was blocked by prior administration of CGRP(8–37), a peptide CGRP antagonist (Williamson et al., Cephalalgia, 1997, 17, 525–531). Trigeminal ganglion stimulation increased facial blood flow in the rat, which was inhibited by CGRP(8–37) (Escott et al., Brain Res. 1995, 669, 93–99). Electrical stimulation of the trigeminal ganglion in marmoset produced an increase in facial blood flow that could be blocked by the non-peptide CGRP antagonist BIBN4096BS (Doods et al., Br. J. Pharmacol., 2000, 129, 420–423). Thus the vascular effects of CGRP may be attenuated, prevented or reversed by a CGRP antagonist.

CGRP-mediated vasodilation of rat middle meningeal artery was shown to sensitize neurons of the trigeminal nucleus caudalis (Williamson et al., The CGRP Family: Calcitonin Gene-Related Peptide (CGRP), Amylin, and Adrenomedullin, Landes Bioscience, 2000, 245–247). Similarly, distention of dural blood vessels during migraine headache may sensitize trigeminal neurons. Some of the associated symptoms of migraine, including extra-cranial pain and facial allodynia, may be the result of sensitized trigeminal neurons (Burstein et al., Ann. Neurol. 2000, 47, 614–624). A CGRP antagonist may be beneficial in attenuating, preventing or reversing the effects of neuronal sensitization.

The ability of the compounds of the present invention to act as CGRP antagonists makes them useful pharmacological agents for disorders that involve CGRP in humans and animals, but particularly in humans. Such disorders include migraine and cluster headache (Doods, Curr Opin Inves Drugs, 2001, 2 (9), 1261–1268; Edvinsson et al., Cephalalgia, 1994, 14, 320–327); chronic tension type headache (Ashina et al., Neurology, 2000, 14, 1335–1340); pain (Yu et al., Eur. J. Pharm., 1998, 347, 275–282); chronic pain (Hulsebosch et al., Pain, 2000, 86, 163–175); neurogenic inflammation and inflammatory pain (Holzer, Neurosci., 1988, 24, 739–768; Delay-Goyet et al., Acta Physiol. Scanda. 1992, 146, 537–538; Salmon et al., Nature Neurosci., 2001, 4(4), 357–358); eye pain (May et al. Cephalalgia, 2002, 22, 195–196), tooth pain (Awawdeh et al., Int. Endocrin. J., 2002, 35, 30–36), non-insulin dependent diabetes mellitus (Molina et al., Diabetes, 1990, 39, 260–265); vascular disorders; inflammation (Zhang et al., Pain, 2001, 89, 265), arthritis, bronchial hyperreactivity, asthma, (Foster et al., Ann. NY Acad. Sci., 1992, 657, 397–404; Schini et al., Am. J. Physiol., 1994, 267, H2483–H2490; Zheng et al., J. Virol., 1993, 67, 5786–5791); shock, sepsis (Beer et al., Crit. Care Med., 2002, 30 (8), 1794–1798); opiate withdrawal syndrome (Salmon et al., Nature Neurosci., 2001, 4(4), 357–358) morphine tolerance (Menard et al., J. Neurosci., 1996, 16 (7), 2342–2351); hot flashes in men and women (Chen et al., Lancet, 1993, 342, 49; Spetz et al., J. Urology, 2001, 166, 1720–1723); allergic dermatitis (Wallengren, Contact Dermatitis, 2000, 43 (3), 137–143); psoriasis; encephalitis, brain trauma, ischaemia, stroke, epilepsy, and neurodegenerative diseases (Rohrenbeck et al., Neurobiol. of Disease 1999, 6, 15–34); skin diseases (Geppetti and Holzer, Eds., Neurogenic Inflammation, 1996, CRC Press, Boca Raton, Fla.), neurogenic cutaneous redness, skin rosaceousness and erythema; tinnitus (Herzog et al., J. Membrane Biology, 2002, 189(3), 225); inflammatory bowel disease, irritable bowel syndrome, (Hoffman et al. Scandinavian Journal of Gastroenterology, 2002, 37(4) 414–422) and cystitis. Of particular importance is the acute or prophylactic treatment of headache, including migraine and cluster headache.

The present invention relates to compounds that are useful as ligands for CGRP receptors, in particular antagonists for CGRP receptors, processes for their preparation, their use in therapy, pharmaceutical compositions comprising them and methods of therapy using them.

SUMMARY OF THE INVENTION

The present invention is directed to compounds which are antagonists of CGRP receptors and which are useful in the treatment or prevention of diseases in which the CGRP is involved, such as migraine. The invention is also directed to pharmaceutical compositions comprising these compounds and the use of these compounds and compositions in the prevention or treatment of such diseases in which CGRP is involved.

DETAILED DESCRIPTION OF THE INVENTION

The present invention is directed to compounds of the formula I:

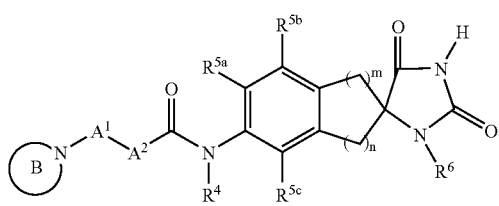

wherein:
B is a heterocycle selected from the group consisting of:

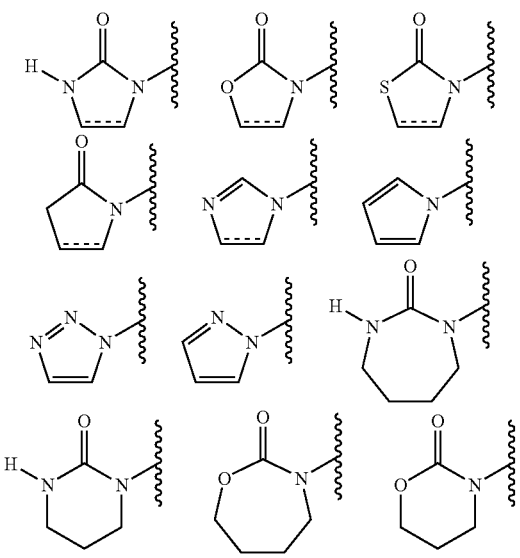

where the dashed line indicates the optional presence of a double bond,
where B is unsubstituted or substituted with 1–5 substituents where the substituents are independently selected from $R^1$, $R^2$, $R^{3a}$ and $R^{3b}$, wherein
$R^1$, $R^2$, $R^{3a}$ and $R^{3b}$ are independently selected from:
(1) —$C_{1-6}$alkyl, which is unsubstituted or substituted with 1–7 substituents where the substituents are independently selected from:
  (a) halo,
  (b) hydroxy,
  (c) —O—$C_{1-6}$alkyl,
  (d) —$C_{3-6}$cycloalkyl,
  (e) phenyl or heterocycle, wherein heterocycle is selected from: pyridyl, pyrimidinyl, pyrazinyl, pyridazinyl, piperidinyl, piperazinyl, pyrrolidinyl, thienyl, or morpholinyl,
    which is unsubstituted or substituted with 1–5 substituents where the substituents are independently selected from:
      (i) —$C_{1-6}$alkyl,
      (ii) —O—$C_{1-6}$alkyl,
      (iii) halo,
      (iv) hydroxy,
      (v) trifluoromethyl, and
      (vi) —$OCF_3$,
  (f) —$CO_2R^9$, wherein $R^9$ is independently selected from:
    (i) hydrogen,
    (ii) —$C_{1-6}$alkyl, which is unsubstituted or substituted with 1–6 fluoro,
    (iii) —$C_{5-6}$cycloalkyl,
    (iv) benzyl, and
    (v) phenyl,
  (g) —$CONR^{10a}R^{11a}$, wherein $R^{10a}$ and $R^{11a}$ are independently selected from:
    (i) hydrogen,
    (ii) —$C_{1-6}$alkyl, which is unsubstituted or substituted with 1–6 fluoro,
    (iii) —$C_{5-6}$cycloalkyl,
    (iv) benzyl,
    (v) phenyl,
    or where $R^{10a}$ and $R^{11a}$ may be joined together to form a ring selected from azetidinyl, pyrrolidinyl, piperidinyl, piperazinyl, or morpholinyl.
(2) —$C_{3-6}$cycloalkyl, which is unsubstituted or substituted with 1–7 substituents where the substituents are independently selected from:
  (a) halo,
  (b) hydroxy,
  (c) —O—$C_{1-6}$alkyl,
  (d) trifluoromethyl, and
  (e) phenyl,
(3) phenyl or heterocycle, wherein heterocycle is selected from: pyridyl, pyrimidinyl, pyrazinyl, thienyl, pyrrolidinyl, thiazolyl, oxazolyl, piperidinyl and morpholinyl, which is unsubstituted or substituted with 1–5 substituents where the substituents are independently selected from:
  (a) —$C_{1-6}$alkyl, which is unsubstituted or substituted with 1–6 fluoro,
  (b) halo,
  (c) hydroxy,
  (d) —O—$C_{1-6}$alkyl, which is unsubstituted or substituted with 1–6 fluoro,
  (e) —$C_{3-6}$cycloalkyl,
  (f) phenyl which is unsubstituted or substituted with 1–5 substituents where the substituents are independently selected from:
    (i) —$C_{1-6}$alkyl,
    (ii) —O—$C_{1-6}$alkyl,
    (iii) halo,
    (iv) hydroxy, and
    (v) trifluoromethyl,
  (g) —$CO_2R^9$,
  (h) —$NR^{10}R^{11}$,
  (i) —$CONR^{10}R^{11}$, and
  (j) —$SO_2R^{12}$,
(4) halo,
(5) hydroxy,
(6) —O—$C_{1-6}$alkyl, which is unsubstituted or substituted with 1–5 halo,
(7) —CN,
(8) —$CO_2R^9$,
(9) —$NR^{10}R^{11}$,
(10) —$SO_2R^{12}$,
(11) —$CONR^{10a}R^{11a}$,
or where $R^{3a}$ and $R^{3b}$ and the carbon atom(s) to which they are attached may be joined together to form a ring selected from cyclobutyl, cyclopentyl, cyclohexyl, azetidinyl, pyrrolidinyl, piperidinyl, or piperazinyl, which is unsubstituted or substituted with 1–5 substituents where the substituents are independently selected from:
(a) —$C_{1-6}$alkyl, which is unsubstituted or substituted with 1–3 substituents where the substituents are independently selected from:
  (i) halo,
  (ii) hydroxy,
  (iii) —O—$C_{1-6}$alkyl,
  (iv) —$C_{3-6}$cycloalkyl,
  (v) phenyl or heterocycle, wherein heterocycle is selected from: pyridyl, pyrimidinyl, pyrazinyl, pyridazinyl, piperidinyl, piperazinyl, pyrrolidinyl, thienyl, or morpholinyl,
  (vi) —$CO_2R^9$,
  (vii) —$NR^{10}R^{11}$,
  (viii) —$SO_2R^{12}$,
  (ix) —$CONR^{10a}R^{11a}$, and
(b) phenyl or heterocycle, wherein heterocycle is selected from: pyridyl, pyrimidinyl, pyrazinyl, thienyl, pyridazinyl, pyrrolidinyl, azetidinyl, piperidinyl and morpholinyl, which is unsubstituted or substituted with 1–3 substituents where the substituents are independently selected from:
  (i) —$C_{1-6}$alkyl, which is unsubstituted or substituted with 1–6 fluoro,
  (ii) halo,
  (iii) hydroxy,
  (iv) —O—$C_{1-6}$alkyl, which is unsubstituted or substituted with 1–6 fluoro, and
  (v) —$C_{3-6}$cycloalkyl,
(c) —$SO_2R^{12}$,
(d) hydroxy,
(e) —O—$C_{1-6}$alkyl, which is unsubstituted or substituted with 1–5 halo,
(f) —$COR^{12}$,
(g) —$NR^{10}R^{11}$, $A^1$ and $A^2$ are independently selected from:
(1) a bond,
(2) —$CR^{13}R^{14}$—, wherein $R^{13}$ and $R^{14}$ are independently selected from:
  (a) hydrogen,
  (b) $C_{1-6}$ alkyl, which is unsubstituted or substituted with 1–6 fluoro, and
  (c) hydroxy,
or wherein one of $A^1$ and $A^2$ is absent;

$R^4$ is selected from:
(1) hydrogen, and
(2) $C_{1-6}$ alkyl, which is unsubstituted or substituted with 1–6 fluoro, $R^{5a}$, $R^{5b}$ and $R^{5c}$ are independently selected from:
(1) hydrogen,
(2) $C_{1-6}$ alkyl,
(3) —O—$C_{1-6}$alkyl,
(4) —$OCF_3$,
(5) trifluoromethyl,
(6) halo,
(7) hydroxy, and
(8) —CN;

$R^6$ is selected from:
(1) hydrogen,
(2) —$C_{1-6}$alkyl which is unsubstituted or substituted with 1–7 substituents where the substituents are independently selected from:
  (a) halo,
  (b) hydroxy,
  (c) —O—$C_{1-6}$alkyl,
  (d) —$C_{3-6}$cycloalkyl, and
  (e) phenyl,
(3) phenyl or heterocycle, wherein heterocycle is selected from: pyridyl, pyrimidinyl, pyrazinyl, or thienyl, which is unsubstituted or substituted with 1–5 substituents where the substituents are independently selected from:
  (a) —$C_{1-6}$alkyl,
  (b) —O—$C_{1-6}$alkyl,
  (c) halo,
  (d) hydroxy, and
  (e) trifluoromethyl;

m is 1 or 2;

n is 1 or 2;

and pharmaceutically acceptable salts thereof and individual enantiomers and diastereomers thereof.

An embodiment of the present invention includes compounds of the formula Ia:

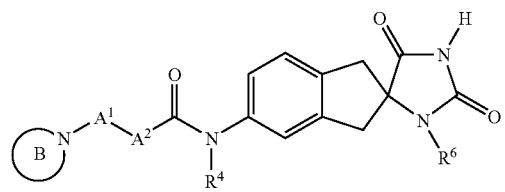

wherein B, $A^1$, $A^2$, $R^4$ and $R^6$ are defined herein;

and pharmaceutically acceptable salts thereof and individual enantiomers and diastereomers thereof.

Another embodiment of the present invention includes compounds of the formula Ib:

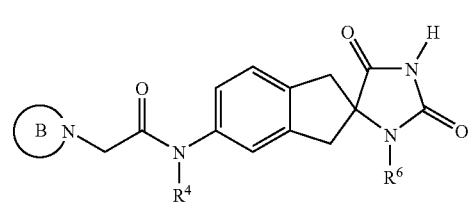

wherein B, $R^4$ and $R^6$ are defined herein;

and pharmaceutically acceptable salts thereof and individual enantiomers and diastereomers thereof.

Another embodiment of the present invention includes compounds of the formula Ic:

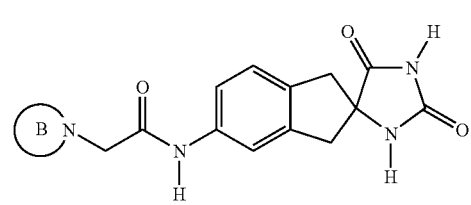

wherein B is defined herein;

and pharmaceutically acceptable salts thereof and individual enantiomers and diastereomers thereof.

Another embodiment of the present invention includes compounds of the formula Id:

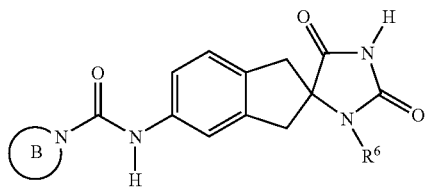

Id wherein B and $R^6$ are defined herein;

and pharmaceutically acceptable salts thereof and individual enantiomers and diastereomers thereof.

Another embodiment of the present invention includes compounds of the formula Ie:

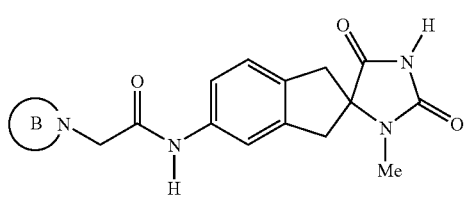

Ie wherein B is defined herein;

and pharmaceutically acceptable salts thereof and individual enantiomers and diastereomers thereof.

Another embodiment of the present invention includes compounds of the formula If:

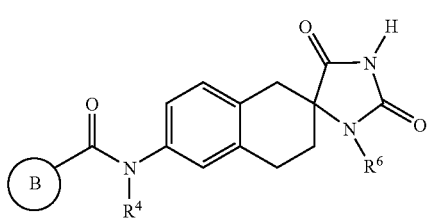

If wherein B, $R^4$ and $R^6$ are defined herein;

and pharmaceutically acceptable salts thereof and individual enantiomers and diastereomers thereof.

In an embodiment of the present invention B is selected from the group consisting of:

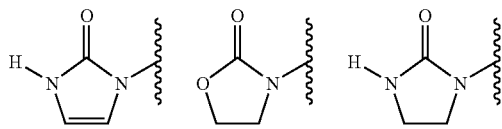

-continued

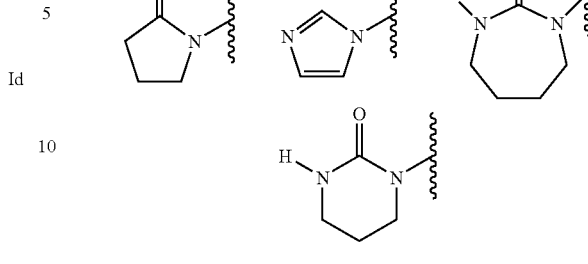

which is unsubstituted or substituted with a substituent selected from $R^1$, $R^2$, $R^{3a}$ and $R^{3b}$, wherein $R^1$, $R^2$, $R^{3a}$ and $R^{3b}$ are defined herein.

In an embodiment of the present invention B is imidazolyl.

In an embodiment of the present invention B is 2-oxo-oxazolinyl.

In an embodiment of the present invention B is 2-oxo-imidazolinyl.

In an embodiment of the present invention B is 2-oxo-1,3-diazepanyl.

In an embodiment of the present invention $R^1$, $R^2$, $R^{3a}$ and $R^{3b}$ are independently selected from:

(1) $C_{1-6}$ alkyl, which is unsubstituted or substituted with 1–5 substituents selected from:
  (a) $C_{3-6}$ cycloalkyl,
  (b) halo, and
  (c) phenyl, and
(2) phenyl, which is unsubstituted or substituted with 1–5 substituents selected from:
  (a) $C_{1-6}$ alkyl,
  (b) —O—$C_{1-6}$ alkyl,
  (c) halo,
  (d) —OH, and
  (e) —$CF_3$, and,
(3) heterocycle, wherein heterocycle is selected from: pyridyl, pyrimidinyl, pyrazinyl, or thienyl, which is unsubstituted or substituted with 1–5 substituents where the substituents are independently selected from:
  (a) $C_{1-6}$ alkyl,
  (b) —O—$C_{1-6}$ alkyl,
  (c) halo,
  (d) —OH, and
  (e) —$CF_3$.

In an embodiment of the present invention $A^1$ is a bond.
In an embodiment of the present invention $A^2$ is —$CH_2$—.
In an embodiment of the present invention $R^4$ is hydrogen.
In an embodiment of the present invention $R^{5a}$, $R^{5b}$ and $R^{5c}$ are independently selected from hydrogen, $C_{1-6}$ alkyl and halo.
In an embodiment of the present invention $R^{5a}$, $R^{5b}$ and $R^{5c}$ are hydrogen.
In an embodiment of the present invention $R^6$ is hydrogen or methyl.
In an embodiment of the present invention m is 1.
In an embodiment of the present invention n is 1.
In an embodiment of the present invention n is 2.

The compounds of the present invention may contain one or more asymmetric centers and can thus occur as racemates and racemic mixtures, single enantiomers, diastereomeric mixtures and individual diastereomers. The compounds of the instant invention have one asymmetric center. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

As appreciated by those of skill in the art, halo or halogen as used herein are intended to include chloro, fluoro, bromo and iodo. Similarly, $C_{1-8}$, as in $C_{1-8}$alkyl is defined to identify the group as having 1, 2, 3, 4, 5, 6, 7 or 8 carbons in a linear or branched arrangement, such that $C_{1-8}$alkyl specifically includes methyl, ethyl, n-propyl, iso-propyl, n-butyl, iso-butyl, tert-butyl, pentyl, hexyl, heptyl and octyl. Likewise, $C_0$, as in $C_0$alkyl is defined to identify the presence of a direct covalent bond. The term "heterocycle" as used herein is intended to include, but is not limited to, the following groups: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxetanyl, pyranyl, pyrazinyl, pyrazolyl, pyridazinyl, pyridopyridinyl, pyridazinyl, pyridyl, pyrinidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives wherein the parent compound is modified by making acid or base salts thereof. Examples of pharmaceutically acceptable salts include, but-are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, fumaric, and tartaric acids. It will be understood that, as used herein, references to the compounds of Formula I are meant to also include the pharmaceutically acceptable salts.

Exemplifying the invention is the use of the compounds disclosed in the Examples and herein. Specific compounds within the present invention include a compound which selected from the group consisting of the compounds disclosed in the following Examples and pharmaceutically acceptable salts thereof and individual diastereomers thereof.

The subject compounds are useful in a method of antagonism of CGRP receptors in a patient such as a mammal in need of such antagonism comprising the administration of an effective amount of the compound. The present invention is directed to the use of the compounds disclosed herein as antagonists of CGRP receptors. In addition to primates, especially humans, a variety of other mammals can be treated according to the method of the present invention.

Another embodiment of the present invention is directed to a method for the treatment, control, amelioration, or reduction of risk of a disease or disorder in which the CGRP receptor is involved in a patient that comprises administering to the patient a therapeutically effective amount of a compound that is an antagonist of CGRP receptors.

The present invention is further directed to a method for the manufacture of a medicament for antagonism of CGRP receptors activity in humans and animals comprising combining a compound of the present invention with a pharmaceutical carrier or diluent:

The subject treated in the present methods is generally a mammal, preferably a human being, male or female, in whom antagonism of CGRP receptor activity is desired. The term "therapeutically effective amount" means the amount of the subject compound that will elicit the biological or medical response of a tissue, system, animal or human that is being sought by the researcher, veterinarian, medical doctor or other clinician. As used herein, the term "treatment" refers both to the treatment and to the prevention or prophylactic therapy of the mentioned conditions, particularly in a patient who is predisposed to such disease or disorder.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention or a prodrug of a compound of the invention to the individual in need of treatment.

The utility of the compounds in accordance with the present invention as antagonists of CGRP receptor activity may be demonstrated by methodology known in the art. Inhibition of the binding of $^{125}$I-CGRP to receptors and functional antagonism of CGRP receptors were determined as follows:

NATIVE RECEPTOR BINDING ASSAY: The binding of $^{125}$I-CGRP to receptors in SK-N-MC cell membranes was carried out essentially as described (Edvinsson et al. (2001) *Eur. J. Pharmacol.* 415, 39–44). Briefly, membranes (25 μg) were incubated in 1 ml of binding buffer [10 mM HEPES, pH 7.4, 5 mM MgCl$_2$ and 0.2% bovine serum albumin (BSA)] containing 10 pM $^{125}$I-CGRP and antagonist. After incubation at room temperature for 3 h, the assay was terminated by filtration through GFB glass fibre filter plates (Millipore) that had been blocked with 0.5% polyethyleneimine for 3 h. The filters were washed three times with ice-cold assay buffer, then the plates were air dried. Scintillation fluid (50 μl) was added and the radioactivity was counted on a Topcount (Packard Instrument). Data analysis was carried out by using Prism and the $K_i$ was determined by using the Cheng-Prusoff equation (Cheng & Prusoff (1973) *Biochem. Pharmacol.* 22, 3099–3108).

NATIVE RECEPTOR FUNCTIONAL ASSAY: SK-N-MC cells were grown in minimal essential medium (MEM) supplemented with 10% fetal bovine serum, 2 mM L-glutamine, 0.1 mM non-essential amino acids, 1 mM sodium pyruvate, 100 units/ml penicillin and 100 μg/ml streptomycin at 37° C., 95% humidity, and 5% CO$_2$. For cAMP assays, cells were plated at $5 \times 10^5$ cells/well in 96-well poly-D-lysine-coated plates (Becton-Dickinson) and cultured for ~18 h before assay. Cells were washed with phosphate-buffered saline (PBS, Sigma) then pre-incubated with 300 μM isobutylmethylxanthine in serum-free MEM for 30 min at 37° C. Antagonist was added and the cells were incubated for 10 min before the addition of CGRP. The incubation was continued for another 15 min, then the cells were washed with PBS and processed for cAMP determination according to the manufacturer's recommended protocol. Maximal stimulation over basal was defined by using 100 nM CGRP. Dose-response curves were generated by using Prism. Dose-ratios (DR) were calculated and used to construct full Schild plots (Arunlakshana & Schild (1959) *Br. J. Pharmacol.* 14, 48–58).

RECOMBINANT RECEPTOR: Human CRLR (Genbank accession number L76380) was subcloned into the expression vector pIRShyg2 (BD Biosciences Clontech) as a 5'NheI and 3' PmeI fragment. Human RAMP1 (Genbank accession number AJ001014) was subcloned into the expression vector pIRESpuro2 (BD Biosciences Clontech) as a 5'NheI and 3'NotI fragment. 293 cells (human embryonic kidney cells; ATCC #CRL-1573) were cultured in DMEM with 4.5 g/L glucose, 1 mM sodium pyruvate and 2 mM glutamine supplemented with 10% fetal bovine serum (FBS), 100 units/mL penicillin and 100 ug/ml streptomycin, and maintained at 37° C. and 95% humidity. Cells were subcultured by treatment with 0.25% trypsin with 0.1% EDTA in HBSS. Stable cell line generation was accomplished by co-transfecting 10 ug of DNA with 30 ug Lipofectamine 2000 (Invitrogen) in 75 cm$^2$ flasks. CRLR and RAMP1 expression constructs were co-taansfected in equal amounts. Twenty-four hours after transfection the cells were diluted and selective medium (growth medium+300 ug/ml hygromycin and 1 ug/ml puromycin) was added the following day. A clonal cell line was generated by single cell deposition utilizing a FACS Vantage SE (Becton Dickinson). Growth medium was adjusted to 150 ug/ml hygromycin and 0.5 ug/ml puromycin for cell propagation.

RECOMBINANT RECEPTOR BINDING ASSAY: Cells expressing recombinant human CRLR/RAMP1 were washed with PBS and harvested in harvest buffer containing 50 mM HEPES, 1 mM EDTA and Complete protease inhibitors (Roche). The cell suspension was disrupted with a laboratory homogenizer and centrifuged at 48,000 g to isolate membranes. The pellets were resuspended in harvest buffer plus 250 mM sucrose and stored at −70° C. For binding assays, 10 ug of membranes were incubated in 1 ml binding buffer (10 mM HEPES, pH 7.4, 5 mM MgCl$_2$, and 0.2% BSA) for 3 hours at room temperature containing 10 pM $^{125}$I-hCGRP (Amersham Biosciences) and antagonist. The assay was terminated by filtration through 96-well GFB glass fiber filter plates (Millipore) that had been blocked with 0.05% polyethyleneimine. The filters were washed 3 times with ice-cold assay buffer (10 mM HEPES, pH 7.4). Scintillation fluid was added and the plates were counted on a Topcount (Packard). Non-specific binding was determined and the data analysis was carried out with the apparent dissociation constant ($K_i$) determined by using a non-linear least squares fitting the bound CPM data to the equation below:

$$Y_{obsd} = \frac{Y_{min} + (Y_{max} - Y_{min})(100 - \% I_{max}/100)}{1 + ([Drug]/K_i(1 + [Radiolabel]/K_d)^{nH}}$$

Where Y is observed CPM bound, Ymax is total bound counts, Y min is non specific bound counts, ($Y_{max}$-Y min) is specific bound counts, % I max is the maximum percent inhibition, % I min is the minimum percent inhibition, radiolabel is the probe, and the $K_d$ is the apparent dissociation constant for the radioligand for the receptor as determined by Hot saturation experiments.

RECOMBINANT RECEPTOR FUNCTIONAL ASSAY: Cells were plated in complete growth medium at 85,000 cells/well in 96-well poly-D-lysine coated plates (Corning) and cultured for ~19 h before assay. Cells were washed with PBS and then incubated with inhibitor for 30 min at 37° C. and 95% humidity in Cellgro Complete Serum-Free/Low-Protein medium (Mediatech, Inc.) with L-glutamine and 1 g/L BSA. Isobutyl-methylxanthine was added to the cells at a concentration of 300 µM and incubated for 30 min at 37° C. Human α-CGRP was added to the cells at a concentration of 0.3 nM and allowed to incubate at 37° C. for 5 min. After α-CGRP stimulation the cells were washed with PBS and processed for cAMP determination utilizing the two-stage assay procedure according to the manufacturer's recommended protocol (cAMP SPA direct screening assay system; RPA 559; Amersham Biosciences). Dose response curves were plotted and $IC_{50}$ values determined from a 4-parameter logistic fit as defined by the equation y=((a−d)/(1+(x/c)$^b$)+d, where y=response, x=dose, a=max response, d=min response, c=inflection point and b=slope.

In particular, the compounds of the following examples had activity as antagonists of the CGRP receptor in the aforementioned assays, generally with a $K_i$ or $IC_{50}$ value of less than about 50 µM. Such a result is indicative of the intrinsic activity of the compounds in use as antagonists of CGRP receptors.

The ability of the compounds of the present invention to act as CGRP antagonists makes them useful pharmacological agents for disorders that involve CGRP in humans and animals, but particularly in humans.

The compounds of the present invention have utility in treating, preventing, ameliorating, controlling or reducing the risk of one or more of the following conditions or diseases: headache; migraine; cluster headache; chronic tension type headache; pain; chronic pain; neurogenic inflammation and inflammatory pain; neuropathic pain; eye pain; tooth pain; diabetes; non-insulin dependent diabetes mellitus; vascular disorders; inflammation; arthritis; bronchial hyperreactivity, asthma; shock; sepsis; opiate withdrawal syndrome; morphine tolerance; hot flashes in men and women; allergic dermatitis; psoriasis; encephalitis; brain trauma; epilepsy; neurodegenerative diseases; skin diseases; neurogenic cutaneous redness, skin rosaceousness and erythema; inflammatory bowel disease, irritable bowel syndrome, cystitis; and other conditions that may be treated or prevented by antagonism of CGRP receptors. Of particular importance is the acute or prophylactic treatment of headache, including migraine and cluster headache.

The subject compounds are further useful in a method for the prevention, treatment, control, amelioration, or reduction of risk of the diseases, disorders and conditions noted herein.

The subject compounds are further useful in a method for the prevention, treatment, control, amelioration, or reduction of risk of the aforementioned diseases, disorders and conditions in combination with other agents.

The compounds of the present invention may be used in combination with one or more other drugs in the treatment, prevention, control, amelioration, or reduction of risk of diseases or conditions for which compounds of Formula I or the other drugs may have utility, where the combination of the drugs together are safer or more effective than either drug alone. Such other drug(s) may be administered, by a route and in an amount commonly used therefor, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy may also include therapies in which the compound of Formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula I.

For example, the present compounds may be used in conjunction with an anti-inflammatory or analgesic agent or an anti-migraine agent, such as an ergotamine or 5-$HT_1$ agonists, especially a 5-$HT_{1B/1D}$ agonist, for example sumatriptan, naratriptan, zolmitriptan, eletriptan, almotriptan, frovatriptan, donitriptan, and rizatriptan; a cyclooxygenase inhibitor, such as a selective cyclooxygenase-2 inhibitor, for example rofecoxib, etoricoxib, celecoxib, valdecoxib or paracoxib; a non-steroidal anti-inflammatory agent or a cytokine-suppressing anti-inflammatory agent, for example with a compound such as aspirin, ibuprofen, ketoprofen, fenoprofen, naproxen, indomethacin, sulindac, meloxicam, piroxicam, tenoxicam, lornoxicam, ketorolac, etodolac, mefenamic acid, meclofenamnic acid, flufenamic acid, tolfenamic acid, diclofenac, oxaprozin, apazone, nimesulide, nabumetone, tenidap, etanercept, tolmetin, phenylbutazone, oxyphenbutazone, diflunisal, salsalate, olsalazine or sulfasalazine and the like; or a steroidal analgesic. Similarly, the instant compounds may be administered with a pain reliever such as acetaminophen, phenacetin, codeine, fentanyl, sufentanil, methadone, acetyl methadol, buprenorphine or morphine.

Additionally, the present compounds may be used in conjunction with an interleukin inhibitor, such as an interleukin-1 inhibitor; an NK-1 receptor antagonist, for example aprepitant; an NMDA antagonist; an NR2B antagonist; a bradykinin-1 receptor antagonist; an adenosine A1 receptor agonist; a sodium channel blocker, for example lamotrigine; an opiate agonist such-as levomethadyl acetate or methadyl acetate; a lipoxygenase inhibitor, such as an inhibitor of 5-lipoxygenase; an alpha receptor antagonist, for example indoramin; an alpha receptor agonist; a vanilloid receptor antagonist; an mGluR5 agonist, antagonist or potentiator; a GABA A receptor modulator, for example acamprosate calcium; nicotinic antagonists or agonists including nicotine; muscarinic agonists or antagonists; a selective serotonin reuptake inhibitor, for example fluoxetine, paroxetine, sertraline, duloxetine, escitalopram, or citalopram; a tricyclic antidepressant, for example amitriptyline, doxepin, protriptyline, desipramine, trimipramine, or imipramine; a leukotriene antagonist, for example montelukast or zafirlukast; an inhibitor of nitric oxide or an inhibitor of the synthesis of nitric oxide.

Also, the present compounds may be used in conjunction with ergot alkaloids, for example ergotamine, ergonovine, ergonovine, methylergonovine, metergoline, ergoloid mesylates, dihydroergotamine, dihydroergocornine, dihydroergocristine, dihydroergocryptine, dihydro-α-ergocryptine, dihydro-β-ergocryptine, ergotoxine, ergocornine, ergocristine, ergocryptine, α-ergocryptine, β-ergocryptine, ergosine, ergostane, bromocriptine, or methysergide.

Additionally, the present compounds may be used in conjunction with a beta-adrenergic antagonist such as timolol, propanolol, atenolol, or nadolol, and the like; a MAO inhibitor, for example phenelzine; a calcium channel blocker, for example flunarizine, nimodipine, lomerizine, verapamil, nifedipine, prochlorperazine or gabapentin; neuroleptics such as olanzapine and quetiapine; an anticonvulsant such as topiramate, zonisamide, tonabersat, carabersat or divalproex sodium; an angiotensin II antagonist, for example losartan and candesartan cilexetil; an angiotensin converting enzyme inhibitor such as lisinopril; or botulinum toxin type A.

The present compounds may be used in conjunction with a potentiator such as caffeine, an H2-antagonist, simethicone, aluminum or magnesium hydroxide; a decongestant such as phenylephrine, phenylpropanolamine, pseudoephedrine, oxymetazoline, epinephrine, naphazoline, xylometazoline, propylhexedrine, or levo-desoxy-ephedrine; an antitussive such as codeine, hydrocodone, caramiphen, carbetapentane, or dextromethorphan; a diuretic; a prokinetic agent such as metoclopramide or domperidone, and a sedating or non-sedating antihistamine.

In a particularly preferred embodiment the present compounds are used in conjunction with an anti-migraine agent, such as: an ergotamine; a 5-HT$_1$ agonist, especially a 5-HT$_{1B/1D}$ agonist, in particular, sumatriptan, naratriptan, zolmitriptan, eletriptan, almotriptan, frovatriptan, donitriptan and rizatriptan; and a cyclooxygenase inhibitor, such as a selective cyclooxygenase-2 inhibitor, in particular, rofecoxib, etoricoxib, celecoxib, meloxicam, valdecoxib or paracoxib.

The above combinations include combinations of a compound of the present invention not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the compound of the present invention to the other active ingredient(s) may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s), and via the same or different routes of administration.

The compounds of the present invention may be administered by oral, parenteral (e.g., intramuscular, intraperitoneal, intravenous, ICV, intracistemal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release. Oral tablets may also be formulated for immediate release, such as fast melt tablets or wafers, rapid dissolve tablets or fast dissolve films.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. Similarly, transdermal patches may also be used for topical administration.

The pharmaceutical composition and method of the present invention may further comprise other therapeutically active compounds as noted herein which are usually applied in the treatment of the above mentioned pathological conditions.

In the treatment, prevention, control, amelioration, or reduction of risk of conditions which require antagonism of CGRP receptor activity an appropriate dosage level will generally be about 0.01 to 500 mg per kg patient body weight per day which can be administered in single or multiple doses. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

When treating, preventing, controlling, ameliorating, or reducing the risk of headache, migraine, cluster headache, or other diseases for which compounds of the present invention are indicated, generally satisfactory results are obtained when the compounds of the present invention are administered at a daily dosage of from about 0.1 milligram to about 100 milligram per kilogram of animal body weight, preferably given as a single daily dose or in divided doses two to six times a day, or in sustained release form. For most large mammals, the total daily dosage is from about 1.0 milligrams to about 1000 milligrams, preferably from about 1 milligrams to about 50 milligrams. In the case of a 70 kg adult human, the total daily dose will generally be from about 7 milligrams to about 350 milligrams. This dosage regimen may be adjusted to provide the optimal therapeutic response.

It will be understood, however, that the specific dose level and frequency of dosage for any particular patient may be varied and will depend upon a variety of factors including the activity of the specific compound employed, the metabolic stability and length of action of that compound, the age, body weight, general health; sex, diet, mode and time of administration, rate of excretion, drug combination, the severity of the particular condition, and the host undergoing therapy.

Several methods for preparing the compounds of this invention are illustrated in the following Schemes and Examples. Starting materials are made according to procedures known in the art or as illustrated herein.

The compounds of the present invention can be prepared readily according to the following Schemes and specific examples, or modifications thereof, using readily available starting materials, reagents and conventional synthesis procedures. In these reactions, it is also possible to make use of variants which are themselves known to those of ordinary skill in this art but are not mentioned in greater detail. The general procedures for making the compounds claimed in this invention can be readily understood and appreciated by one skilled in the art from viewing the following Schemes.

The synthesis of spirohydantoin intermediates may be conducted as described in Schemes 1–4. Spirohydantoin intermediates bearing $R^{5a}$, $R^{5b}$ and $R^{5c}$ may be prepared by employing appropriately substituted starting materials or by derivatization of any intermediates and/or final products as desired by methods known in the art.

Commercially available 6-bromo-2-tetralone (1) may be readily converted to the spirohydantoin 2 under Bucherer-Bergs conditions, using ammonium carbonate and either sodium cyanide or potassium cyanide. Other 2-tetralones may be readily accessed using a variety of literature methods, such as the Friedel-Crafts reaction of arylacetyl chlorides with ethene as described by Burckhalter and Campbell, *J. Org. Chem.*, 26, 4232 (1961), and converted to the corresponding spirohydantoins analogously. In Scheme 1, treatment of spirohydantoin 2 with ethyl magnesium bromide followed by tert-butyllithium effects metal-halogen exchange and the resulting aryllithium species is quenched with carbon dioxide to give acid 3. A Schmidt reaction of 3 with hydrazoic acid may be used to provide aniline 4, as reviewed by Wolff, *Org. React.*, 3, 307 (1946). Alternatively, a modified Curtius rearrangement using 3 and diphenylphosphoryl azide according to the procedure of Yamada and coworkers, *Tetrahedron*, 30, 2151 (1974), can provide aniline 4 via either its tert-butyl or benzyl carbamate derivatives.

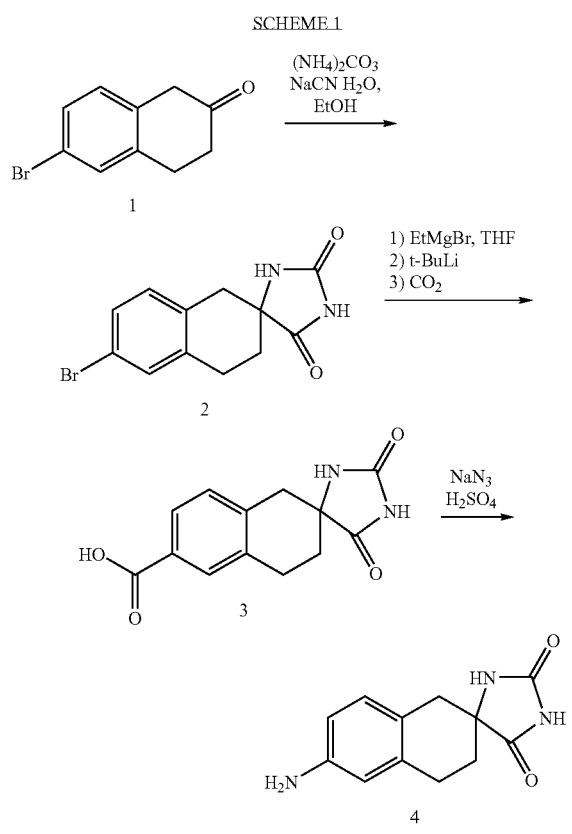

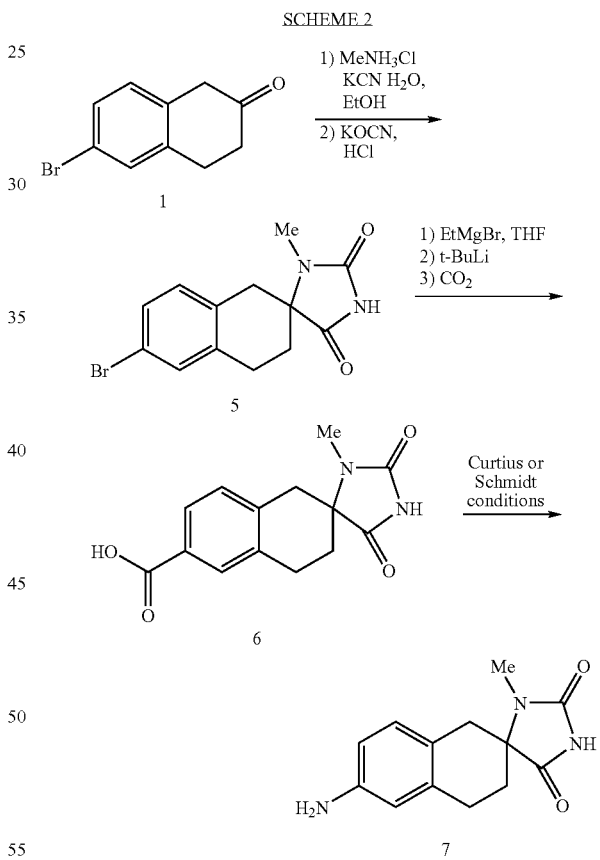

In Scheme 2, treatment of 6-bromo-2-tetralone (1) with methylamine hydrochloride and potassium cyanide, followed by potassium cyanate and hydrochloric acid, provides the methylated hydantoin derivative 5. Analogous procedures to those described in Scheme 1 may be used to provide acid 6 and aniline 7.

Scheme 3 illustrates a route to 7-substituted tetralin derivatives 10 and 11. 3-Bromophenylacetic acid is converted to the corresponding acid chloride and this is subjected to Friedel—Crafts reaction with ethene, affording the 7-bromo-2-tetralone 9. This intermediate may be elaborated using the procedures described in Scheme 1 to provide the acid (10) and aniline (11).

SCHEME 3

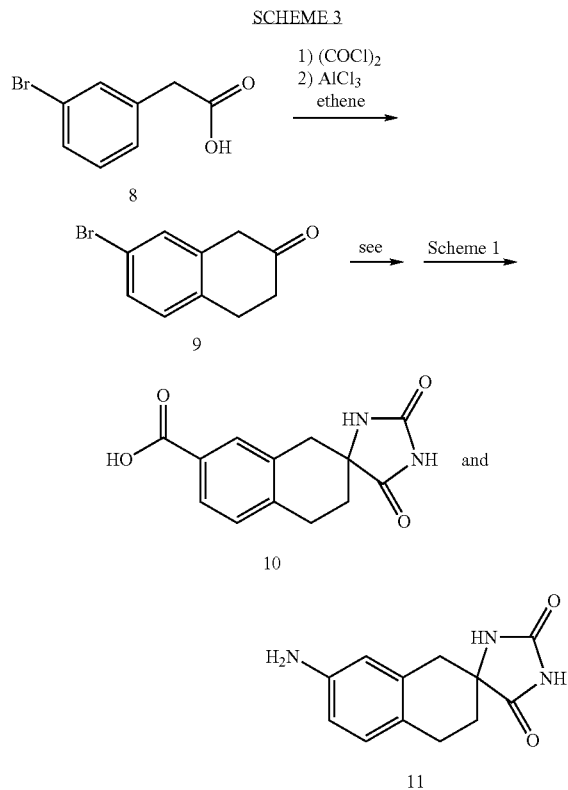

Scheme 4 details the synthesis of the key indane-based spirohydantoin intermediates.

SCHEME 4

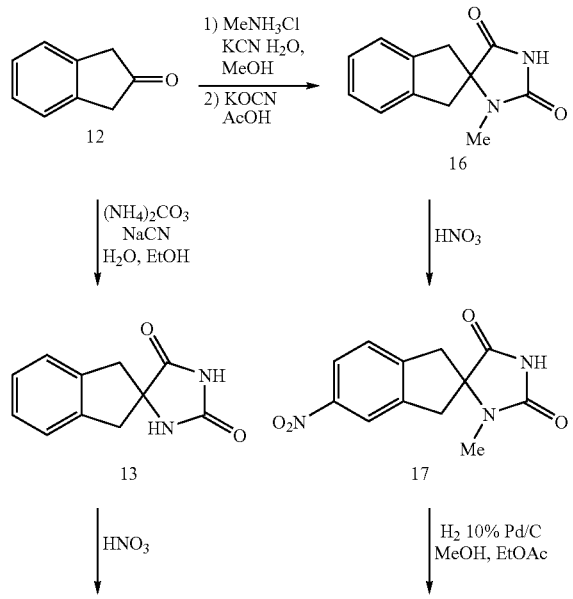

2-Indanone (12) is converted to the spirohydantoin 13 via Bucherer-Bergs chemistry as shown. Treatment of 13 with nitric acid provides the 5-nitroindane derivative 14, which may be-reduced to the corresponding aniline 15 under catalytic hydrogenation conditions. Alternatively, a two-step process can be employed to convert 2-indanone (12) into the N-methylspirohydantoin 16. Treatment of 12 with potassium cyanide and methylamine hydrochloride affords an amino nitrile which is converted to the spirohydantoin 16 using potassium cyanate and acetic acid. Subjection of 16 to the nitration-reduction sequence used for 13 leads to the corresponding aniline 18, as detailed in Scheme 4.

Spirohydantoin intermediates may be resolved to give pure enantiomers using techniques familiar to those skilled in the art. For example, chromatography of the nitro intermediate 17 on a ChiralPak AD column can be used to provide the individual enantiomers (+)-17 and (−)-17, and these enantiomers may be reduced to the corresponding anilines [(+)-18 and (−)-18] by catalytic hydrogenation. Use of standard coupling procedures using enantiomerically pure anilines affords the individual enantiomers of the final products. Resolution may be effected by other methodologies, such as fractional crystallization of diastereomeric salts, and it may be carried out on other synthetic intermediates or on the final products. Alternatively, an assymetric synthesis of a key intermediate, such as an amino acid precursor of a spirohydantoin, could be used to provide an enantiomerically enriched final product.

Spirohydantoin aniline intermediates, such as those described in Schemes 1–4, may be coupled with a variety of carboxylic acids, or carboxylic acid derivatives, to provide amide final products.

SCHEME 5

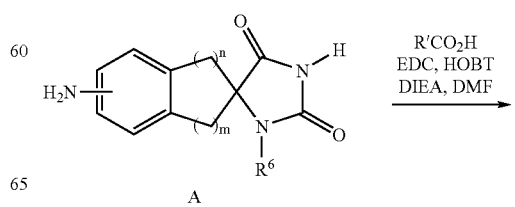

-continued

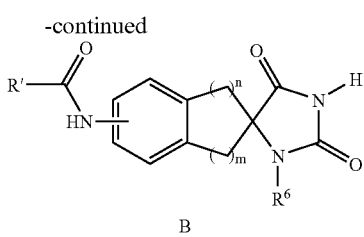

B

Thus, coupling of amine A in Scheme 5 with a carboxylic acid, R'CO$_2$H, can be used to give amide B. Other standard coupling conditions may be employed in the synthesis of such amides, such as use of an alternative coupling reagent like PyBOP, or activation of the carboxylic acid as an acid anhydride or acid chloride. Ureas may also be synthesized from aniline A and an appropriate amine by use of phosgene, 1,1'-carbonyldiimidazole, 4-nitrophenyl chloroformate, or a similar reagent.

Most of the acids (R'CO$_2$H), used to make the compounds of the present invention are readily available. They may be obtained from commercial sources or synthesized by methodology familiar to those skilled in the art and as described in the chemical literature. A number of the acids were synthesized using the methodology outlined in Scheme 6.

SCHEME 6

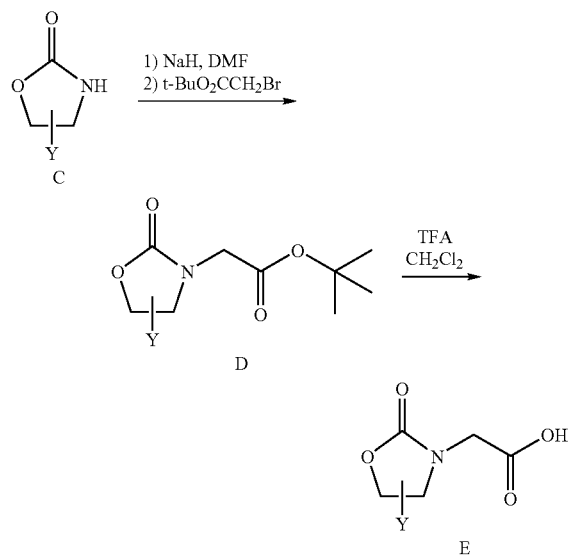

In Scheme 6, the oxazolidinone C is treated with sodium hydride, then tert-butyl bromoacetate, to provide ester D. Standard deprotection using trifluoroacetic acid affords the acid intermediate E, which may be used for coupling to amines like A to give compounds of the present invention. Simple modifications of this methodology, including different protecting group strategies and the use of heterocycles other then a oxazolidinone, may be used to provide other acids of interest, such as those detailed in Table 2 (vide infra). For example, an imidazolone may be used in place of the oxazolidinone in Scheme 6 and by application of well-precedented methodology, such as alkylation or arylation reactions, to such molecules a variety of other acids are provided.

In some cases the final product may be further modified, for example, by manipulations of substituents. These manipulations may include, but are not limited to, reduction, oxidation, allylation, acylation, and hydrolysis reactions which are commonly known to those skilled in the art.

In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

Intermediate 1

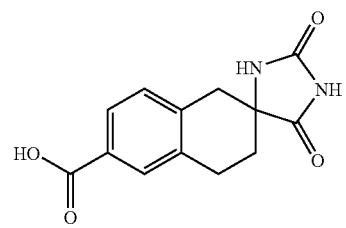

(±)-6'-Carboxy-3',4'-dihydro-1'H-spiro[imidazolidine-4,2'-naphthalene]-2,5-dione Step A. (±)-6'-Bromo-3',4'-dihydro-1'H-spiro[imidazolidine-4,2'-naphthalene]-2,5-dione A stirred mixture of 6-bromo-2-tetralone (17.6 g, 78.2 mmol), sodium cyanide (9.58 g, 195 mmol), and ammonium carbonate (97.7 g, 1.02 mol) in H$_2$O (100 mL) and EtOH (100 mL) was heated to 70° C. for 3 h, then allowed to cool to ambient temperature. The precipitate was collected by filtration and washed with H$_2$O (5×200 mL). Drying in vacuo afforded the title compound as a pale solid. MS: m/z=297 (M+1).

Step B. (±)-6'-Carboxy-3',4'-dihydro-1'H-spiro[imidazolidine-4,2'-naphthalene]-2,5-dione To a stirred suspension of (±)-6'-bromo-3',4'-dihydro-1'H-spiro[imidazolidine-4,2'-naphthalene]-2,5-dione (14.9 g, 50.5 mmol) in THF (1.2 L), at −70° C., was added dropwise ethyl magnesium bromide (3.0 M in THF, 51 mL, 152 mmol). The resulting mixture was stirred for 10 min, then tert-butyllithium (1.7 M in pentane, 180 mL, 305 mmol) was added dropwise over 30 min. Stirring was continued at −70° C. for 20 min, then additional tert-butyllithium (1.7 M in pentane, 60 mL, 102 mmol) was added dropwise over 10 min. After a further 30 min, CO$_{2(g)}$ was bubbled into the reaction mixture until LCMS analysis indicated complete reaction. The mixture was allowed to warm slowly to ambient temperature and the THF was removed in vacuo. The residue was suspended in H$_2$O and the solution was adjusted to pH=1–2 by the addition of conc. hydrochloric acid, to a final volume of about 500 mL. The mixture was filtered and the isolated solid was washed with H$_2$O (4×100 mL) then dried in vacuo. Trituration of this crude solid with EtOH provided the title compound as a pale tan solid. MS: m/z=261 (M+1).

Intermediate 2

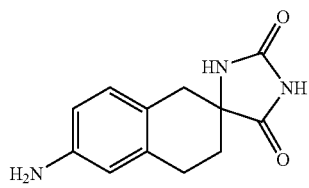

(±)-6'-Amino-3',4'-dihydro-1'H-spiro[imidazolidine-4,2'-naphthalene]-2,5-dione

Step A. (±)-6'-Amino-3',4'-dihydro-1'H-spiro[imidazolidine-4,2'-naphthalene]-2,5-dione A stirred mixture of (±)-6'-carboxy-3',4'-dihydro-1'H-spiro[imidazolidine-4,2'-naphthalene]-2,5-dione (described in Intermediate 1) (1.50 g, 5.76 mmol), and sodium azide (749 mg, 11.53 mmol) in conc. $H_2SO_4$ (30 mL) was heated to 50° C. for 2 h, then allowed to cool to ambient temperature. The mixture was adjusted to pH 8 by addition of 6 N aqueous NaOH and concentrated in vacuo to precipitate a solid. The precipitate was collected by filtration and washed extensively with $H_2O$. Drying in vacuo afforded the title compound as a light brown solid. MS: m/z=232 (M+1).

Intermediate 3

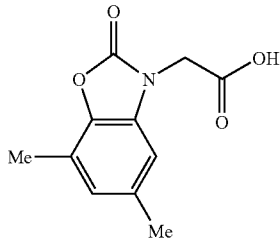

(5,7-Dimethyl-2-oxo-1,3-benzoxazol-3(2H)-yl)acetic acid

Step A. 5,7-Dimethyl-2-benzoxazolinone

A mixture of 2-amino-4,6-dimethylphenol (412 mg, 3.00 mmol) and 1,1'-carbonyldiimidazole (730 mg, 4.50 mmol) in THF (15 mL) was heated at reflux for 3 h. The mixture was allowed to cool, and the solvent removed under reduced pressure. The residue was taken up in EtOAc and washed with 1.0 N aqueous HCl (2×), then brine, then the EtOAc was dried over $Na_2SO_4$, filtered, and concentrated in vacuo to give the title compound. MS: m/z=164 (M+1).

Step B. tert-Butyl (5,7-dimethyl-2-oxo-1,3-benzoxazol-3(2H)-yl)acetate

To a stirred solution of 5,7-dimethyl-2-benzoxazolinone (200 mg, 1.23 mmol) in DMF (2 mL) was added sodium hydride (59 mg of a 60% dispersion in mineral oil, 1.47 mmol). The mixture was stirred at ambient temperature for 10 min, then tert-butyl bromoacetate (287 mg, 1.47 mmol) was added and stirring was continued for 2 h. The reaction mixture was quenched with $H_2O$ and purified directly by HPLC using a reversed phase C18 column and eluting with a gradient of $H_2O:CH_3CN:CF_3CO_2H$—90:10:0.1 to 5:95:0.1. Lyophilization provided the title compound. MS: m/z=222 (M–$C_4H_7$).

Step C. (5,7-Dimethyl-2-oxo-1,3-benzoxazol-3(2H)-yl)acetic acid

A solution of the tert-butyl (5,7-dimethyl-2-oxo-1,3-benzoxazol-3(2H)-yl)acetate from Step B in $CH_2Cl_2$ (0.7 mL) and $CF_3CO_2H$ (0.3 mL) was stood at ambient temperature for 2 h. Toluene (5 mL) was added and the mixture was conc. in vacuo to give the title compound as a dark solid. MS: m/z=222 (M+1).

Intermediates 4–7

Essentially following the procedures outlined for Intermediate 3, the compounds listed in Table 1 were prepared. The requisite starting materials were commercially available, described in the literature, or readily synthesized by one skilled in the art of organic synthesis. In some cases, straightforward protecting group strategies were applied.

TABLE 1

| Intermediate | $R^c$ | MS (M + 1) |
|---|---|---|
| 4 | (4-benzyl-oxazolidin-2-one-3-yl)methyl | 236 |
| 5 | (4-isopropyl-oxazolidin-2-one-3-yl)methyl | 188 |
| 6 | (5-phenyl-oxazolidin-2-one-3-yl)methyl | 222 |
| 7 | (4-phenyl-oxazolidin-2-one-3-yl)methyl | 222 |

Intermediate 8

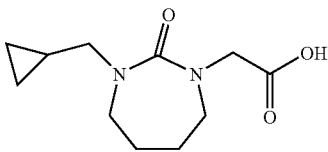

[3-(Cyclopropylmethyl)-2-oxo-1,3-diazepan-1-yl]
acetic acid

Step A. N-(Cyclopropylmethyl)prop-2-en-1-amine

Cyclopropanecarboxaldehyde (1.00 g, 14.3 mmol) was added dropwise to a stirred solution of allylamine (4.07 g, 71.3 mmol) in MeOH (100 mL) and stirring was continued at ambient temperature for 2 h, then sodium cyanoborohydride (0.94 g, 15.0 mmol) was added. After 3 h, the solvent was removed under reduced pressure. The crude product was purified by silica gel chromatography, eluting with a gradient of $CH_2Cl_2$:MeOH:$NH_4OH$—100:0:0 to 90:10:1 to provide the title compound as a yellow oil. MS: m/z=112 (M+1).

Step B. tert-Butyl N-allyl-N-{[allyl(cyclopropylmethyl)amino]carbonyl}glycinate To an ice-cooled solution of tert-butyl N-allylglycinate (Senokuchi et al. *J. Med. Chem.* 1995, 38, 2521) (308 mg, 1.80 mmol) in anhydrous THF (10 mL) was added phosgene (0.89 mL of a 20% solution in toluene, 1.80 mmol), then triethylamine (0.25 mL, 1.80 mmol). The resulting solution was stirred at 0° C. for 1 h, then N-(cyclopropylmethyl)prop-2-en-1-amine (200 mg, 1.80 mmol) was added, followed by triethylamine (0.75 mL, 5.40 mmol). The reaction mixture was allowed to warm to ambient temperature and stirring was continued for 18 h. The solvent was removed under reduced pressure and the residue was partitioned between EtOAc and water. The organic layer was dried over $Na_2SO_4$, filtered, and concentrated in vacuo to give a crude product, which was purified by silica gel chromatography, eluting with a gradient of hexane:EtOAc—100:0 to 90:10 to provide the title compound. MS: m/z=309 (M+1).

Step C. tert-Butyl [3-(cyclopropylmethyl)-2-oxo-2,3,4,7-tetrahydro-1H-1,3-diazepin-1-yl]acetate A stirred mixture of tert-butyl N-allyl-N-{[allyl(cyclopropylmethyl)-amino]carbonyl}glycinate (287 mg, 0.93 mmol) and bis(tricyclohexylphosphine)-benzylidene ruthenium (IV) dichloride (Grubbs' catalyst) (192 mg, 0.23 mmol) in anhydrous $CH_2Cl_2$ (90 mL) was heated to 40° C. for 2 h. An additional portion of bis(tricyclohexylphosphine)benzylidene ruthenium (IV) dichloride (80 mg, 0.097 mmol) was added and the reaction mixture was heated to 40° C. for a further 2 h. The resulting mixture was filtered and the filtrate was concentrated under reduced pressure. The crude product was purified by silica gel chromatography, eluting with a gradient of hexane:EtOAc—100:0 to 70:30 to provide the title compound. MS: m/z=225 (M–$C_4H_7$).

Step D. tert-Butyl [3-(cyclopropylmethyl)-2-oxo-1,3-diazepan-1-yl]acetate

To a solution of tert-butyl [3-(cyclopropylmethyl)-2-oxo-2,3,4,7-tetrahydro-1H-1,3-diazepin-1-yl]acetate (250 mg, 0.89 mmol) in EtOH (10 mL) was added 10% Pd/C (9.5 mg) and the reaction stirred vigorously under hydrogen (ca. 1 atm). After 90 min, the catalyst was filtered off and the filtrate was concentrated to yield the title compound as a pale brown solid. MS: m/z=283 (M+1).

Step E. [3-(Cyclopropylmethyl)-2-oxo-1,3-diazepan-1-yl]acetic acid

A solution of tert-butyl [3-(cyclopropylmethyl)-2-oxo-1,3-diazepan-1-yl]acetate (240 mg, 0.85 mmol) in $CH_2Cl_2$ (5 mL) and $CF_3CO_2H$ (2 mL) was stirred at ambient temperature for 3 h. The mixture was concentrated in vacuo and the residue was purified by HPLC using a reversed phase C18 column and eluting with a gradient of $H_2O$:$CH_3CN$:$CF_3CO_2H$—90:10:0.1 to 5:95:0.1. Lyophilization provided the title compound as a clear oil. MS: m/z=227 (M+1).

Intermediate 9

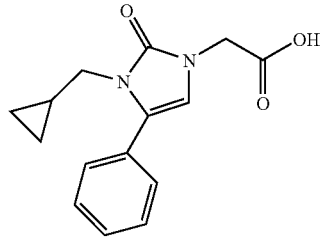

[3-(Cyclopropylmethyl)-2-oxo-4-phenyl-2,3-dihydro-1H-imidazol-1-yl]acetic acid

Step A. 4-Phenylimidazol-2-one

Potassium cyanate (2.00 g, 24.7 mmol) was added in portions, over 15 min, to a stirred solution of 2-aminoacetophenone hydrochloride (3.85 g, 22.4 mmol) in water (130 mL) at 70° C., while the pH of the solution was maintained at pH 1 to 3 by addition of conc. hydrochloric acid. The reaction mixture was stirred at 70° C. for 4 h, then allowed to cool to ambient temperature and stood for 18 h. The title compound was isolated by filtration as a white solid. MS: m/z=161 (M+1).

Step B. tert-Butyl (2-oxo-4-phenyl-2,3-dihydro-1H-imidazol-1-yl)acetate

To a stirred solution of 4-phenylimidazol-2-one (1.00 g, 6.24 mmol) in DMF (10 mL) at 0° C. was added sodium hydride (300 mg of a 60% dispersion in mineral oil, 7.49 mmol). The mixture was stirred at 0° C. for 1 h, then tert-butyl bromoacetate (1.47 g, 7.49 mmol) was added. The reaction mixture was allowed to warm to ambient temperature and stirring was continued for 18 h. The reaction mixture was poured into water and extracted with $CH_2Cl_2$ (3×). The combined organic extracts were dried over $Na_2SO_4$, filtered, and concentrated in vacuo to give a crude product, which was purified by silica gel chromatography, eluting with a gradient of $CH_2Cl_2$:MeOH:$NH_4OH$—100:0:0 to 90:5:0.5 to provide the title compound. MS: m/z=275 (M+1).

Step C. tert-Butyl [3-(cyclopropylmethyl)-2-oxo-4-phenyl-2,3-dihydro-1H-imidazol-1-yl]acetate A stirred mixture of tert-butyl (2-oxo-4-phenyl-2,3-dihydro-1H-imidazol-1-yl)acetate (107 mg, 0.39 mmol), cyclopropylmethyl bromide (105 mg, 0.78 mmol), and cesium carbonate (153 mg, 0.47 mmol) in acetone (5 mL) was heated at reflux for 3 days. The reaction mixture was concentrated under reduced pressure, partitioned between brine and $CH_2Cl_2$, and extracted with $CH_2Cl_2$ (3×). The combined organic extracts were dried over $Na_2SO_4$, filtered, and concentrated in vacuo. The crude product was purified by silica gel chromatography, eluting with a gradient of hexane:BtOAc—100:0 to 50:50 to provide the title compound. MS: m/z=273 (M–$C_4H_7$).

Step D. [3-(Cyclopropylmethyl)-2-oxo-4-phenyl-2,3-dihydro-1H-imidazol-1-yl]acetic acid A solution of tert-butyl [3-(cyclopropylmethyl)-2-oxophenyl-2,3-dihydro-1H-imidazol-1-yl]acetate (41 mg, 0.125 mmol) in $CH_2Cl_2$ (2 mL) and $CF_3CO_2H$ (1 mL) was stirred at ambient temperature for 3 h. The mixture was concentrated in vacuo to afford the title compound. MS: m/z=273 (M+1).

Intermediate 10

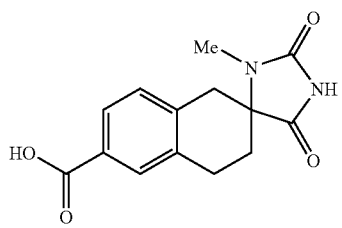

(±)-6'-Carboxy-3-methyl-3',4'-dihydro-1'H-spiro[imidazolidine-4,2'-naphthalene]-2,5-dione

Step A. (±)-6'-Bromo-3-methyl-3',4'-dihydro-1'H-spiro[imidazolidine-4,2'-naphthalene]-2,5-dione A mixture of 6-bromo-2-tetralone (1.00 g, 4.44 mmol) and methylamine hydrochloride (300 mg, 4.44 mol) in $H_2O$ (1 mL) and EtOH (1.5 mL) was stirred at ambient temperature for 20 min. Potassium cyanide (289 mg, 4.44 mmol) was added and stirring was continued for 18 h. The mixture was added dropwise to a stirred solution of 1.0 N aqueous HCl (4.5 mL) at 0° C., then potassium cyanate (360 mg, 4.44 mmol) was added portionwise. The stirred mixture was heated to 95° C. and conc. hydrochloric acid (0.44 mL) was added dropwise. The reaction mixture was heated at this temperature for 1 h, allowed to cool, and extracted with $CH_2Cl_2$ (80 mL). The organic extract was dried over $Na_2SO_4$, filtered, and concentrated to dryness. The crude product was purified by silica gel chromatography, eluting with a gradient of $CH_2Cl_2$:MeOH—100:0 to 90:10 to provide a crude sample of the title compound (ca. 70% pure). Trituration with EtOH afforded the title compound as a pale solid. MS: m/z=311 (M+1).

Step B. (±)-6'-Carboxy-3-methyl-3',4'-dihydro-1'H-spiro[imidazolidine-4,2'-naphthalene]-2,5-dione To a stirred suspension of (±)-6'-bromo-3-methyl-3',4'-dihydro-1'H-spiro[imidazolidine-4,2'-naphthalene]-2,5-dione (211 mg, 0.682 mmol) in THF (30 mL), at –70° C., was added dropwise ethyl magnesium bromide (1.0 M in THF, 1.37 mL, 1.37 mmol). The resulting mixture was stirred for 15 min, then tert-butyllithium (1.7 M in pentane, 1.61 mL, 2.73 mmol) was added dropwise. After a further 30 min, $CO_{2\,(g)}$ was bubbled into the reaction mixture until LCMS analysis indicated complete reaction. The mixture was allowed to warm slowly to ambient temperature and the THF was removed in vacuo. The residue was suspended in $H_2O$ (20 mL) and the solution was adjusted to pH=1–2 by the addition of 1.0 N hydrochloric acid, then it was saturated with $NaCl_{(s)}$. The mixture was filtered and the isolated solid was washed with $H_2O$ then dried in vacuo. Trituration of this crude solid with EtOH provided the title compound as a pale tan solid. MS: m/z=275 (M+1).

Intermediate 11

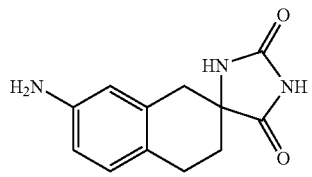

(±)-7'-Amino-3',4'-dihydro-1'H-spiro[imidazolidine-4,2'-naphthalene]-2,5-dione

Step A. 7-Bromo-2-tetralone

A solution of 3-bromophenylacetic acid (10.4 g, 48.4 mmol) in oxalyl chloride (50 mL, 0.57 mol) was stirred at ambient temperature for 5 min then at reflux for 5 h. The oxalyl chloride was removed in vacuo and the residue was dissolved in anhydrous $CH_2Cl_2$ (100 mL). This solution was added dropwise to a rapidly stirred, ice-cooled solution of $AlCl_3$ (23.2 g, 174.2 mmol) in $CH_2Cl_2$ (500 mL). A stream of ethylene gas was blown into the vortex of the stirred solution during the addition and the reaction temperature was kept at <5° C. The reaction mixture was allowed to warm to ambient temperature and then poured onto ice and stirred vigorously. The organic portion was removed and the aqueous layer extracted with $CH_2Cl_2$ (2×200 mL). The combined $CH_2Cl_2$ fractions were passed through a 2" pad of silica and concentrated to give a thick, red oil. The crude product was purified by silica gel chromatography, eluting with a gradient of hexane:EtOAc—100:0 to 75:25 to provide the title compound as a pale yellow solid. MS: m/z=226 (M+1).

Step B. (±)-7'-Amino-3',4'-dihydro-1'H-spiro[imidazolidine-4,2'-naphthalene]-2,5-dione Essentially following the procedures described for Intermediate 1 and Intermediate 2, but using 7-bromo-2-tetralone in place of 6-bromo-2-tetralone, (±)-7'-amino-3',4'-dihydro-1'H-spiro[imidazolidine-4,2'-naphthalene]-2,5-dione was prepared. MS: m/z=232 (M+1).

Intermediate 12

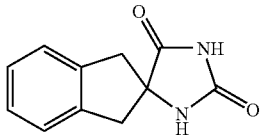

(±)-Spiro[imidazolidine-4,2'-indane]-2,5-dione

Step A. (±)-Spiro[imidazolidine-4,2'-indane]-2,5-dione

A stirred mixture of 2-indanone (3.0 g, 22.6 mmol), sodium cyanide (3.3 g, 67.3 mmol), and ammonium carbonate (22 g, 228 mol) in $H_2O$ (50 mL) and EtOH (50 mL) was heated to 70° C. for 3 h, then allowed to cool to ambient temperature. The precipitate was collected by filtration and washed with $H_2O$ (5×100 mL). Drying in vacuo afforded the title compound as a gray-brown solid. MS: m/z=202 (M+1).

Intermediate 13

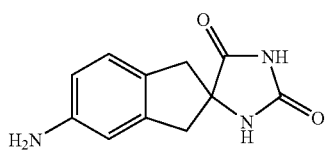

(±)-5'-Amino-spiro[imidazolidine-4,2'-indane]-2,5-dione

Step) A. (±)-5'-Nitro-spiro[imidazolidine-4,2'-indane]-2,5-dione

A solution of (±)-spiro[imidazolidine-4,2'-indane]-2,5-dione (3.0 g, 14.8 mmol, described in Intermediate 12) in conc. nitric acid (33 mL) was stirred at ambient temperature for 1 h. The reaction was then poured onto crushed ice and the resultant solid was isolated by filtration. The crude material was recrystallized from ethanol to give the title compound as a yellow solid. MS: m/z=248 (M+1).

Step B. (±)-5'-Amino-spiro[imidazolidine-4,2'-indane]-2,5-dione

To a suspension of (±)-5'-nitro-spiro[imidazolidine-4,2'-indane]-2,5-dione (1.77 g, 7.16 mmol) in EtOAc (100 mL) and MeOH (100 mL) was added 10% Pd/C (400 mg) and the reaction stirred vigorously under hydrogen (ca. 1 atm). After 1 h, the catalyst was filtered off and the filtrate was concentrated to yield the title compound as a pale brown solid. MS: m/z=218 (M+1).

Intermediate 14

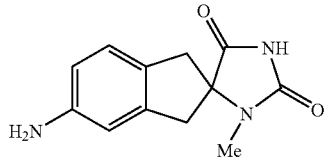

(+)-5'-Amino-3-methyl-spiro[imidazolidine-4,2'-indane]-2,5-dione

Step A. 2-(Methylamino)indane-2-carbonitrile hydrochloride

To a mixture of 2-indanone (20.0 g, 151 mmol) in MeOH (20 mL) was added methylamine hydrochloride (10.2 g, 151 mmol). To the stirred mixture was added $H_2O$ (20 mL) and a fine homogenous slurry developed. The reaction mixture was cooled to 0° C. and KCN (9.84 g, 151 mmol) in $H_2O$ (20 mL) was added slowly over 30 min, such that the temperature did not exceed 10° C., then stirring was continued at ambient temperature for 18 h. The reaction mixture was extracted with $Et_2O$ (250 mL) and the organic extract was washed with brine (50 mL) then dried over $MgSO_4$. HCl (g) was bubbled through the vigorously stirred solution for 10 minutes and a white solid precipitated. The solid was filtered, washed with $Et_2O$, and dried to yield the title compound. MS: m/z=173 (M+1).

Step B. (±)-3-Methyl-spiro[imidazolidine-4,2'-indane]-2,5-dione

To a stirred mixture of 2-(methylamino)indane-2-carbonitrile hydrochloride from Step A (6.0 g, 28.8 mmol) in AcOH (45 mL) was added a solution of potassium cyanate (4.65 g, 57 mmol) in $H_2O$ (6 mL) and the reaction mixture was stirred for 1 h. The mixture was poured into cold $H_2O$ (150 mL) and the precipitate was isolated by filtration, washed with $H_2O$ and air dried. The crude solid was suspended in 1 N HCl (30 mL) and stirred to 50° C. for 2 h. The reaction mixture was cooled, filtered, and the isolated solid washed with $H_2O$ and dried in vacuo to yield the title compound. MS: m/z=217 (M+1).

Step C. (±)-3-Methyl-5'-nitro-spiro[imidazolidine-4,2'-indane]-2,5-dione

To stirred fuming nitric acid (100 ml) was slowly added (±)-3-methyl-spiro[imidazolidine-4,2'-indane]-2,5-dione (4.5 g, 20.9 mmol) in portions over 30 min. The reaction mixture was diluted with $H_2O$ (200 mL) and the precipitate was collected by filtration, washed with $H_2O$ and dried in vacuo to give the title compound. MS: m/z=262 (M+1).

Step D. (±)-5'-Amino-3-methyl-spiro[imidazolidine-4,2'-indane]-2,5-dione

Essentially following the procedures described for Intermediate 13, but using (±)-3-methyl-5'-nitro-spiro[imidazolidine-4,2'-indane]-2,5-dione in place of (±)-5'-nitro-spiro[imidazolidine-4,2'-indane]-2,5-dione, the title compound was prepared. MS: m/z=232 (M+1).

Intermediate 15

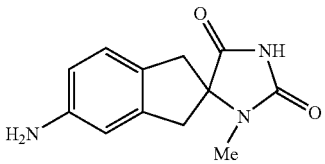

(−)-5'-Amino-3-methyl-spiro[imidazolidine-4,2'-indane]-2,5-dione

Step A. (−)-3-Methyl-5'-nitro-spiro[imidazolidine-4,2'-indane]-2,5-dione (±)-3-Methyl-5'-nitro-spiro[imidazolidine-4,2'-indane]-2,5-dione (described in Intermediate 14) was dissolved in a mixture of MeOH, CH₃CN and diethylamine and the enantiomers were resolved by HPLC, utilizing a ChiralPak AD column and eluting with CH₃CN:MeOH—90:10. The first major peak to elute was (+)-3-methyl-5'-nitro-spiro[imidazolidine-4,2'-indane]-2,5-dione and the second major peak to elute was (−)-3-methyl-5'-nitro-spiro[imidazolidine-4,2'-indane]-2,5-dione, the title compound. MS: m/z=262 (M+1).

Step B. (−)-5'-Amino-3-methyl-spiro[imidazolidine-4,2'-indane]-2,5-dione

Essentially following the procedures described for Intermediate 13, but using (−)-3-methyl-5'-nitro-spiro[imidazolidine-4,2'-indane]-2,5-dione in place of (±)-5'-nitro-spiro[imidazolidine-4,2'-indane]-2,5-dione, the title compound was prepared. MS: m/z=232 (M+1).

Intermediate 16

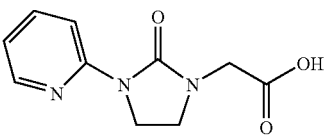

(2-Oxo-3-pyridin-2-ylimidazolidin-1-yl)acetic acid

Step A. 1-Pyridin-2-ylimidazolidin-2-one

A mixture of 2-imidazolidinone (1.00 g, 11.6 mmol), 2-bromopyridine (3.40 mL, 34.8 mmol), copper powder (2.58 g, 40.7 mmol), CuCl (230 mg, 2.32 mmol), and KOAc (3.99 g, 40.7 mmol) in pyridine (10 mL) was heated at 60° C. for 18 h. The cooled mixture was partitioned between CHCl₃ (100 mL) and 10% aqueous citric acid (50 mL). The aqueous layer was adjusted to pH 11 with 10 N aqueous NaOH, extracted with CHCl₃ (3×100 mL), and these organic layers were combined and dried over Na₂SO₄, filtered, and concentrated under reduced pressure, to give the title compound in sufficient purity for use in the next step. MS: m/z=164 (M+1).

Step B. tert-Butyl (2-oxo-3-pyridin-2-ylimidazolidin-1-yl)acetate

To a stirred mixture of 1-pyridin-2-ylimidazolidin-2-one from Step A (150 mg, 0.92 mmol) and tert-butyl bromoacetate (197 mg, 1.01 mmol) in DMF (2 mL) at 0° C. was added sodium hydride (40 mg of a 60% dispersion in mineral oil, 1.00 mmol). The mixture was stirred at 0° C. for 30 min, then quenched with saturated aqueous NaHCO₃ and extracted with CHCl₃ (2×35 mL). The combined organic layers were dried over Na₂SO₄, filtered, and concentrated under reduced pressure. The crude product was purified by silica gel chromatography, eluting with a gradient of hexane:EtOAc—100:0 to 70:30, to give the title compound. MS: m/z=278 (M+1).

Step C. (2-Oxo-3-pyridin-2-ylimidazolidin-1-yl)acetic acid

A solution of tert-butyl 2-oxo-3-pyridin-2-ylimidazolidin-1-yl)acetate from Step B (150 mg, 0.54 mmol) in EtOAc (10 mL) at 0° C. was saturated with HCl (g). The mixture was stood at 0° C. for a total of 30 min, then concentrated in vacuo to give the title compound as a white solid. MS: m/z=222 (M+1).

EXAMPLE 1

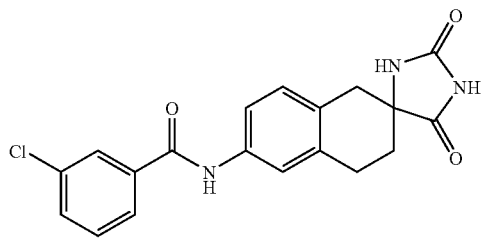

(±)-6'-[(3—Chlorobenzoyl)amino]-3',4'-dihydro-1'H-spiro[imidazolidine-4,2'-naphthalene]-2,5-dione A mixture of 3-chlorobenzoic acid (11 mg, 0.067 mmol), (±)-6'-amino-3',4'-dihydro-1'H-spiro[imidazolidine-4,2'-naphthalene]-2,5-dione (described in Intermediate 2) (13 mg, 0.056 mmol), EDC (13 mg, 0.067 mmol), HOBT (10 mg, 0.067 mmol), and N,N-diisopropylethylamine (0.012 mL, 0.067 mmol) was stirred in DMF (0.3 mL) at ambient temperature for 18 h. The crude mixture was purified directly by HPLC using a reversed phase C18 column and eluting with a gradient of H₂O:CH₃CN:CF₃CO₂H—90:10:0.1 to 5:95:0.1. Lyophilization provided the title compound as a white solid. MS: m/z=370 (M+1). HRMS: m/z=370.0957; calculated m/z=370.0953 for C₁₉H₁₇ClN₃O₃.

EXAMPLES 2–3

Essentially following the procedures outlined for Example 1, the compounds listed in Table 2 were prepared. The requisite carboxylic acids were commercially available, described in the literature, synthesized according to methodology described herein (vide supra), or readily synthesized by one skilled in the art of organic synthesis. In some cases, straightforward protecting group strategies were applied.

TABLE 2

[Structure: spiro tetrahydronaphthalene-imidazolidine-2,4-dione with R<sup>b</sup>NH substituent]

| Example | R<sup>b</sup> | MS (M + 1) |
|---|---|---|
| 2 | [4-benzyl-oxazolidin-2-one-N-CH<sub>2</sub>C(O)-] | 449 |
| 3 | [4-isopropyl-oxazolidin-2-one-N-CH<sub>2</sub>C(O)-] | 401 |

EXAMPLES 4–8

Essentially following the procedures outlined for Example 1, but using Intermediate 13 in place of Intermediate 2, the compounds listed in Table 3 were prepared. The requisite carboxylic acids were commercially available, described in the literature, synthesized according to methodology described herein (vide supra), or readily synthesized by one skilled in the art of organic synthesis. In some cases, straightforward protecting group strategies were applied.

TABLE 3

[Structure: spiro[imidazolidine-4,2'-indane]-2,5-dione with R<sup>b</sup>NH substituent]

| Example | R<sup>b</sup> | MS (M + 1) |
|---|---|---|
| 4 | [cyclopropylmethyl-1,3-diazepan-2-one-N-CH<sub>2</sub>C(O)-] | 440 |

TABLE 3-continued

| Example | R<sup>b</sup> | MS (M + 1) |
|---|---|---|
| 5 | [4-phenyl-imidazol-1-yl-CH<sub>2</sub>C(O)-] | 402 |
| 6 | [5-phenyl-oxazolidin-2-one-N-CH<sub>2</sub>C(O)-] | 421 |
| 7 | [4-phenyl-oxazolidin-2-one-N-CH<sub>2</sub>C(O)-] | 421 |
| 8 | [1-cyclopropylmethyl-5-phenyl-imidazol-2(3H)-one-3-yl-CH<sub>2</sub>C(O)-] | 472 |

EXAMPLE 9

[Structure of final compound]

3-Methyl-5'-{[2-(2-oxo-3-pyridin-2-ylimidazolidin-1-yl)acetyl]amino}-spiro[imidazolidine-4,2'-indane]-2,5-dione, enantiomer B Essentially following the procedures outlined for Example 1, but using Intermediate 15 in place of Intermediate 2, and Intermediate 16 in place of 3-chlorobenzoic acid, the title compound was prepared. MS: m/z=435 (M+1). HRMS: m/z=435.1788; calculated m/z=435.1776 for $C_{22}H_{23}N_6O_4$.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in responsiveness of the mammal being treated for any of the indications with the compounds of the invention indicated above.

What is claimed is:

1. A compound of the formula I:

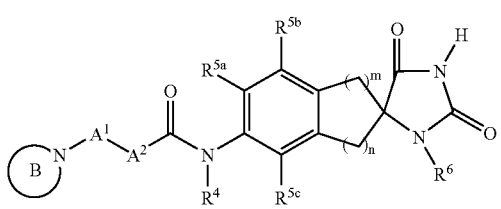

wherein:

B is a heterocycle selected from the group consisting of:

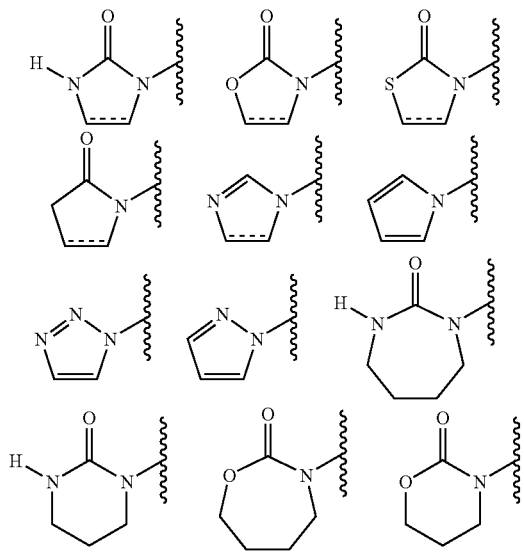

where the dashed line indicates the optional presence of a double bond, where B is unsubstituted or substituted with 1–5 substituents where the substituents are independently selected from $R^1$, $R^2$, $R^{3a}$ and $R^{3b}$, wherein $R^1$, $R^2$, $R^{3a}$ and $R^{3b}$ are independently selected from:

(1) —$C_{1-6}$alkyl, which is unsubstituted or substituted with 1–7 substituents where the substituents are independently selected from:
  (a) halo,
  (b) hydroxy,
  (c) —O—$C_{1-6}$alkyl,
  (d) —$C_{3-6}$cycloalkyl,
  (e) phenyl or heterocycle, wherein heterocycle is selected from: pyridyl, pyrimidinyl, pyrazinyl, pyridazinyl, piperidinyl, piperazinyl, pyrrolidinyl, thienyl, or morpholinyl,
  which is unsubstituted or substituted with 1–5 substituents where the substituents are independently selected from:
    (i) —$C_{1-6}$alkyl,
    (ii) —O—$C_{1-6}$alkyl,
    (iii) halo,
    (iv) hydroxy,
    (v) trifluoromethyl, and
    (vi) —$OCF_3$,
  (f) —$CO_2R^9$, wherein $R^9$ is independently selected from:
    (i) hydrogen,
    (ii) —$C_{1-6}$alkyl, which is unsubstituted or substituted with 1–6 fluoro,
    (iii) —$C_{5-6}$cycloalkyl,
    (iv) benzyl, and
    (v) phenyl,
  (g) —$CONR^{10a}R^{11a}$, wherein $R^{10a}$ and $R^{11a}$ are independently selected from:
    (i) hydrogen,
    (ii) —$C_{1-6}$alkyl, which is unsubstituted or substituted with 1–6 fluoro,
    (iii) —$C_{5-6}$cycloalkyl,
    (iv) benzyl,
    (v) phenyl,
    or where $R^{10a}$ and $R^{11a}$ may be joined together to form a ring selected from azetidinyl, pyrrolidinyl, piperidinyl, piperazinyl, or morpholinyl.

(2) —$C_{3-6}$cycloalkyl, which is unsubstituted or substituted with 1–7 substituents where the substituents are independently selected from:
  (a) halo,
  (b) hydroxy,
  (c) —O—$C_{1-6}$alkyl,
  (d) trifluoromethyl, and
  (e) phenyl, (3) phenyl or heterocycle, wherein heterocycle is selected from: pyridyl, pyrimidinyl, pyrazinyl, thienyl, pyrrolidinyl, thiazolyl, oxazolyl, piperidinyl and morpholinyl, which is unsubstituted or substituted with 1–5 substituents where the substituents are independently selected from:
  (a) —$C_{1-6}$alkyl, which is unsubstituted or substituted with 1–6 fluoro,
  (b) halo,
  (c) hydroxy,
  (d) —O—$C_{1-6}$alkyl, which is unsubstituted or substituted with 1–6 fluoro,
  (e) —$C_{3-6}$cycloalkyl,
  (f) phenyl which is unsubstituted or substituted with 1–5 substituents where the substituents are independently selected from:
    (i) —$C_{1-6}$alkyl,
    (ii) —O—$C_{1-6}$alkyl,
    (iii) halo,
    (iv) hydroxy, and
    (v) trifluoromethyl,
  (g) —$CO_2R^9$,
  (h) —$NR^{10}R^{11}$,
  (i) —$CONR^{10}R^{11}$, and
  (j) —$SO_2R^{12}$, (4) halo,
(5) hydroxy,
(6) —O—$C_{1-6}$alkyl, which is unsubstituted or substituted with 1–5 halo,
(7) —CN,
(8) —$CO_2R^9$;

(9) —NR$^{10}$R$^{11}$,
(10) —SO$_2$R$^{12}$,
(11) —CONR$^{10a}$R$^{11a}$,
or where R$^{3a}$ and R$^{3b}$ and the carbon atom(s) to which they are attached may be joined together to form a ring selected from cyclobutyl, cyclopentyl, cyclohexyl, azetidinyl, pyrrolidinyl, piperidinyl, or piperazinyl, which is unsubstituted or substituted with 1–5 substituents where the substituents are independently selected from:
  (a) —C$_{1-6}$alkyl, which is unsubstituted or substituted with 1–3 substituents where the substituents are independently selected from:
    (i) halo,
    (ii) hydroxy,
    (iii) —O—C$_{1-6}$alkyl,
    (iv) —C$_{3-6}$cycloalkyl,
    (v) phenyl or heterocycle, wherein heterocycle is selected from: pyridyl, pyrimidinyl, pyrazinyl, pyridazinyl, piperidinyl, piperazinyl, pyrrolidinyl, thienyl, or morpholinyl,
    (vi) —CO$_2$R$^9$,
    (vii) —NR$^{10}$R$^{11}$,
    (viii) —SO$_2$R$^{12}$,
    (ix) —CONR$^{10a}$R$^{11a}$, and
  (b) phenyl or heterocycle, wherein heterocycle is selected from: pyridyl, pyrimidinyl, pyrazinyl, thienyl, pyridazinyl, pyrrolidinyl, azetidinyl, piperidinyl and morpholinyl, which is unsubstituted or substituted with 1–3 substituents where the substituents are independently selected from:
    (i) —C$_{1-6}$alkyl, which is unsubstituted or substituted with 1–6 fluoro,
    (ii) halo,
    (iii) hydroxy,
    (iv) —O—C$_{1-6}$alkyl, which is unsubstituted or substituted with 1–6 fluoro, and
    (v) —C$_{3-6}$cycloalkyl,
  (c) —SO$_2$R$^{12}$,
  (d) hydroxy,
  (e) —O—C$_{1-6}$alkyl, which is unsubstituted or substituted with 1–5 halo,
  (f) —COR$^{12}$,
  (g) —NR$^{10}$R$^{11}$,
A$^1$ and A$^2$ are independently selected from:
  (1) a bond,
  (2) —CR$^{13}$R$^{14}$—, wherein R$^{13}$ and R$^{14}$ are independently selected from:
    (a) hydrogen,
    (b) C$_{1-6}$ alkyl, which is unsubstituted or substituted with 1–6 fluoro, and
    (c) hydroxy,
  or wherein one of A$^1$ and A$^2$ is absent;
R$^4$ is selected from:
  (1) hydrogen, and
  (2) C$_{1-6}$ alkyl; which is unsubstituted or substituted with 1–6 fluoro,
R$^{5a}$, R$^{5b}$ and R$^{5c}$ are independently selected from:
  (1) hydrogen,
  (2) C$_{1-6}$ alkyl,
  (3) —O—C$_{1-6}$alkyl,
  (4) —OCF$_3$,
  (5) trifluoromethyl,
  (6) halo,
  (7) hydroxy, and
  (8) —CN;

R$^6$ is selected from:
  (1) hydrogen,
  (2) —C$_{1-6}$alkyl which is unsubstituted or substituted with 1–7 substituents where the substituents are independently selected from:
    (a) halo,
    (b) hydroxy,
    (c) —O—C$_{1-6}$alkyl,
    (d) —C$_{3-6}$cycloalkyl, and
    (e) phenyl,
  (3) phenyl or heterocycle, wherein heterocycle is selected from: pyridyl, pyrimidinyl, pyrazinyl, or thienyl, which is unsubstituted or substituted with 1–5 substituents where the substituents are independently selected from:
    (a) —C$_{1-6}$alkyl,
    (b) —O—C$_{1-6}$alkyl,
    (c) halo,
    (d) hydroxy, and
    (e) trifluoromethyl;
m is 1 or 2;
n is 1 or 2;
and pharmaceutically acceptable salts thereof and individual enantiomers and diastereomers thereof.

2. The compound of claim 1 of the formula:

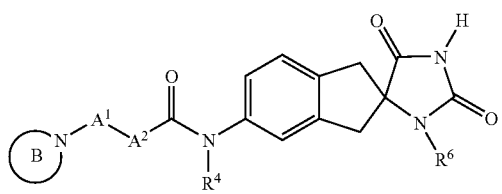

and pharmaceutically acceptable salts thereof and individual enantiomers and diastereomers thereof.

3. The compound of claim 1 of the formula:

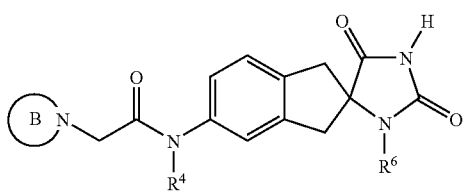

and pharmaceutically acceptable salts thereof and individual enantiomers and diastereomers thereof.

4. The compound of claim 1 of the formula:

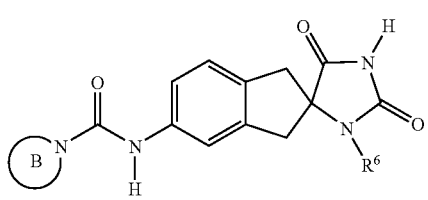

and pharmaceutically acceptable salts thereof and individual enantiomers and diastereomers thereof.

5. The compound of claim 1 of the formula:

and pharmaceutically acceptable salts thereof and individual enantiomers and diastereomers thereof.

6. The compound of claim 1 of the formula:

and pharmaceutically acceptable salts thereof and individual enantiomers and diastereomers thereof.

7. The compound of claim 1 wherein B is selected from the group consisting of:

which is unsubstituted or substituted with a substituent selected from $R^1$, $R^2$, $R^{3a}$.

8. The compound of claim 1 wherein B is selected from imidazolyl, 2-oxo-oxazolinyl, 2-oxo-imidazolinyl, and 2-oxo-1,3-diazepanyl.

9. The compound of claim 1 wherein $R^1$, $R^2$, $R^{3a}$ and $R^{3b}$ are independently selected from:
(1) $C_{1-6}$ alkyl, which is unsubstituted or substituted with 1–5 substituents selected from:
 (a) $C_{3-6}$cycloalkyl,
 (b) halo, and
 (c) phenyl, and
(2) phenyl, which is unsubstituted or substituted with 1–5 substituents selected from:
 (a) $C_{1-6}$alkyl,
 (b) —O—$C_{1-6}$alkyl,
 (c) halo,
 (d) —OH, and
 (e) —$CF_3$, and,
(3) heterocycle, wherein heterocycle is selected from: pyridyl, pyrimidinyl, pyrazinyl, or thienyl, which is unsubstituted or substituted with 1–5 substituents where the substituents are independently selected from:
 (a) $C_{1-6}$alkyl,
 (b) —O—$C_{1-6}$alkyl,
 (c) halo,
 (d) —OH, and
 (e) —$CF_3$.

10. The compound of claim 1 wherein $A^1$ is a bond.

11. The compound of claim 1 wherein $A^2$ is —$CH_2$—.

12. The compound of claim 1 wherein $R^4$ is hydrogen.

13. The compound of claim 1 wherein $R^{5a}$, $R^{5b}$ and $R^{5c}$ are independently selected from hydrogen, $C_{1-6}$alkyl and halo.

14. The compound of claim 1 wherein $R^6$ is hydrogen or methyl.

15. A compound selected from:

-continued

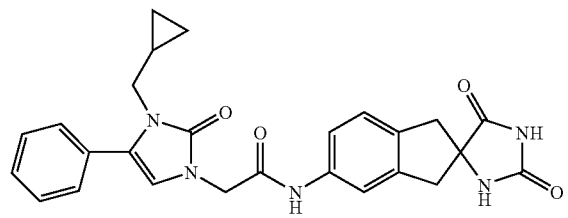
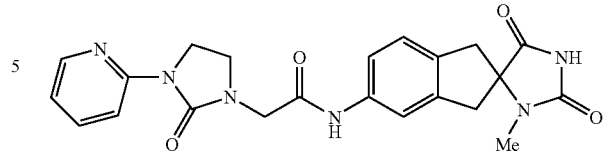
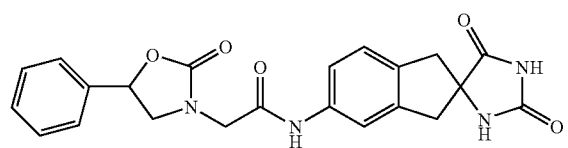

and pharmaceutically acceptable salts thereof and individual enantiomers and diastereomers thereof.

16. A pharmaceutical composition which comprises an inert carrier and the compound of claim 1.

17. A method of treating migraine headaches or cluster headaches, said method comprising the administration, to a person in need of such treatment, of a therapeutically effective amount of the compound of claim 1.

* * * * *